US010308711B2

(12) United States Patent
Liang et al.

(10) Patent No.: US 10,308,711 B2
(45) Date of Patent: Jun. 4, 2019

(54) HEAVY CHAIN ONLY ANTIBODIES TO PDGF

(71) Applicant: Allergan, Inc., Irvine, CA (US)

(72) Inventors: Yanbin Liang, Tustin, CA (US); Daniel W. Gil, Corona Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/234,817

(22) Filed: Aug. 11, 2016

(65) Prior Publication Data

US 2017/0044247 A1 Feb. 16, 2017

Related U.S. Application Data

(60) Provisional application No. 62/333,772, filed on May 9, 2016, provisional application No. 62/205,191, filed on Aug. 14, 2015.

(51) Int. Cl.
*C07K 16/22* (2006.01)

(52) U.S. Cl.
CPC .......... *C07K 16/22* (2013.01); *C07K 2317/24* (2013.01); *C07K 2317/52* (2013.01); *C07K 2317/522* (2013.01); *C07K 2317/565* (2013.01); *C07K 2317/569* (2013.01); *C07K 2317/64* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| RE30,985 E | 6/1982 | Cartaya | |
| 4,485,045 A | 11/1984 | Regen | |
| 4,496,689 A | 1/1985 | Mitra | |
| 4,544,545 A | 10/1985 | Ryan et al. | |
| 4,560,655 A | 12/1985 | Baker | |
| 4,640,835 A | 2/1987 | Shimizu et al. | |
| 4,657,866 A | 4/1987 | Kumar | |
| 4,670,417 A | 6/1987 | Iwasaki et al. | |
| 4,767,704 A | 8/1988 | Cleveland et al. | |
| 4,791,192 A | 12/1988 | Nakagawa et al. | |
| 4,927,762 A | 5/1990 | Darfler | |
| 5,013,556 A | 5/1991 | Woodle et al. | |
| 5,122,469 A | 6/1992 | Mather et al. | |
| 5,204,244 A | 4/1993 | Fell et al. | |
| 5,534,615 A | 7/1996 | Baker et al. | |
| 5,869,079 A | 2/1999 | Wong et al. | |
| 6,797,492 B2 | 9/2004 | Daugherty et al. | |
| 6,884,879 B1 | 4/2005 | Baca et al. | |
| 7,090,681 B2 | 8/2006 | Weber et al. | |
| 7,117,096 B2 | 10/2006 | Luo et al. | |
| 7,297,334 B2 | 11/2007 | Baca et al. | |
| 8,409,577 B2 * | 4/2013 | Thompson | C07K 16/18 424/134.1 |
| 8,466,263 B2 * | 6/2013 | Marasco | A61K 51/1045 530/388.26 |
| 8,502,014 B2 | 8/2013 | Grosveld | |
| 8,507,748 B2 | 8/2013 | Grosveld | |
| 8,735,551 B2 * | 5/2014 | Garner | A61K 39/39558 424/141.1 |
| 8,791,244 B2 * | 7/2014 | Daly | C07K 16/32 530/388.1 |
| 8,883,150 B2 | 11/2014 | Craig et al. | |
| 8,921,522 B2 | 12/2014 | Grosveld et al. | |
| 8,921,524 B2 | 12/2014 | Grosveld et al. | |
| 8,945,552 B2 | 2/2015 | Baehner et al. | |
| 2009/0142343 A1 | 6/2009 | Fuh et al. | |
| 2009/0307787 A1 | 12/2009 | Grosveld et al. | |
| 2010/0159587 A1 | 6/2010 | Brinkmann et al. | |
| 2011/0118444 A1 | 5/2011 | Grosveld et al. | |
| 2013/0259868 A1 | 10/2013 | Roschke et al. | |
| 2013/0323235 A1 | 12/2013 | Craig et al. | |
| 2013/0344057 A1 | 12/2013 | Grosveld et al. | |
| 2014/0033335 A1 | 1/2014 | Grosveld | |
| 2014/0037616 A1 | 2/2014 | Grosveld | |
| 2014/0134176 A1 * | 5/2014 | Arch | C07K 16/22 424/139.1 |
| 2014/0356908 A1 | 12/2014 | Grosveld et al. | |
| 2015/0175689 A1 | 6/2015 | Fuh et al. | |

FOREIGN PATENT DOCUMENTS

| | | |
|---|---|---|
| WO | 198700195 A1 | 1/1987 |
| WO | 199003430 A1 | 4/1990 |
| WO | 199845331 A2 | 10/1998 |
| WO | 2004-058820 | 7/2004 |
| WO | 2005087812 A1 | 9/2005 |
| WO | 2009-058383 | 5/2009 |

(Continued)

OTHER PUBLICATIONS

Campochiaro, Peter, Ocular Neovascularization, J Mol Med, 2013, 311-321, 91.
Dugel, Pravin et al, Anti-PDGF Combination Therapy in Neovascular Age-Related Macular Degeneration: Results of a Phase 2b Study, Retina Today, 2013, 65-71.
Jain, Maneesh et al, Engineering Antibodies for Clinical Applications, Trends in Biotechnology, 2007, 307-316, 25 (7).
Mabry, Robert et al, A Dual Targeting PDGERβ/VEGF-A Molecule Assembled From Stable Antibody Fragments Demonstrates Anti-Angiogenic Activity in Vitro and in Vivo, MABS, 2010, 20-34, 2(1).
Patent Cooperation Treaty, Notification of Transmittal of the International Search Report & The Written Opinion of the International Searching Authority, or the Declaration, PCT/US2016/046595, dated Oct. 26, 2016, pp. 1-18.
Sadiq, Mohammad Ali et al, Platelet Derived Growth Factor Inhibitors: A Potential Therapeutic Approach for Ocular Neovascularization, Saudi Journal of Ophthalmology, 2015, 287-291, 29.

(Continued)

*Primary Examiner* — Marianne P Allen
(74) *Attorney, Agent, or Firm* — Brigitte C. Phan

(57) ABSTRACT

Disclosed herein are monospecific HCAb antibodies with antigen-binding specificity to PDGF and bispecific antibodies with antigen-binding specificities to PDGF-2 and VEGF or to PDGF and ANG-2.

7 Claims, 5 Drawing Sheets

Specification includes a Sequence Listing.

(56) References Cited

FOREIGN PATENT DOCUMENTS

WO    2009-120922    10/2009
WO    2012-131078    10/2012
WO    2014072876 A1  5/2014

OTHER PUBLICATIONS

Spaide, Richard, Rationale for Combination Therapy in Age-Related Macular Dengeration, Retina, 2009, S2-S4, 29.

* cited by examiner

HEAVY CHAIN ONLY ANTIBODIES TO PDGF

CROSS-REFERENCE TO RELATED APPLICATIONS

This application claims the benefit of U.S. Provisional Application No. 62/205,191 filed on Aug. 14, 2015, and U.S. Provisional Application No. 62/333,772 filed on May 9, 2016. The entire contents of both of the foregoing applications are incorporated herein by reference.

BACKGROUND

Angiogenesis, the formation of new blood vessels from preexisting vasculature, is a major component in several retinal vascular diseases causing blindness, such as retinopathy of prematurity, proliferative diabetic retinopathy, diabetic macular edema, and age-related macular degeneration. Ocular neovascularization is the abnormal or excessive formation of blood vessels in the eye. Ocular neovascularization has been shown to be relevant in both diabetic retinopathy and age-related macular degeneration.

Age-related macular degeneration (AMD) is a leading cause of blindness in the elderly population and is recognized as dry and wet AMD forms. The dry, or nonexudative, form involves both atrophic and hypertrophic changes of the retinal pigment epithelium (RPE). The dry form is characterized by macular drusen which are pigmented areas containing dead cells and metabolic products that distort the retina and eventually cause loss of acute vision. Patients with nonexudative AMD (dry form) can progress to the wet, or exudative or neovascular, AMD, in which pathologic choroidal neovascular membranes (CNVM) develop under the retina, leak fluid and blood, and, ultimately, cause a centrally blinding disciform scar over a relatively short time frame if left untreated. Choroidal neovascularization (CNV), the growth of new blood vessels from the choroid capillary network across the Bruch's membrane/RPE interface into the neural retina, results in retinal detachment, subretinal and intraretinal edema, and scarring.

Diabetes can affect the eye in a number of ways. Diabetic retinopathy (DR) is a complication of diabetes that results from damage to the blood vessels of the light-sensitive tissue at the back of the eye (the retina). At first, diabetic retinopathy may cause no symptoms or only mild vision problems. Eventually, however, diabetic retinopathy can result in blindness. Diabetic macular edema (DME) is the swelling of the retina in diabetes mellitus due to leaking of fluid from blood vessels within the macula.

SUMMARY

Disclosed herein are monospecific heavy chain only antibodies (HCAb) having specificity for PDGF and bispecific antibodies having specificity for PDGF and ANG-2 or VEGF.

Thus, in some embodiments, heavy chain only antibodies (HCAb) are disclosed with an antigen-binding specificity for PDGF. In certain embodiments, an HCAb has the variable heavy chain (VH) sequence of one of SEQ ID NOs:10, 14, 18, 22, 26, 30, 34, 38, 42, 46, or 50. In other embodiments, the HCAb VH region has at least 85% identity to the variable region sequence of one of SEQ ID NOs: 10, 14, 18, 22, 26, 30, 34, 38, 42, 46, or 50.

In yet other embodiments, one or more of the complementarity determining regions (CDR) of the HCAb are selected from SEQ ID NOs:11-13, 15-17, 19-21, 23-25, 27-29, 31-33, 35-37, 39-41, 43-45, 47-49, and 51-53. In other embodiments, the HCAb CDRs have at least 85% identity to the CDR sequences selected from SEQ ID NOs: 11-13, 15-17, 19-21, 23-25, 27-29, 31-33, 35-37, 39-41, 43-45, 47-49, and 51-53.

In some embodiments, the HCAb with antigen-binding specificity for PDGF-BB comprises CDRs of SEQ ID NOs: 11-13. In some embodiments, the HCAb with antigen-binding specificity for PDGF-BB comprises CDRs of SEQ ID NOs:15-17. In some embodiments, the HCAb with antigen-binding specificity for PDGF-BB comprises CDRs of SEQ ID NOs:19-21. In some embodiments, the HCAb with antigen-binding specificity for PDGF-BB comprises CDRs of SEQ ID NOs:23-25. In some embodiments, the HCAb with antigen-binding specificity for PDGF-BB comprises CDRs of SEQ ID NOs:27-29. In some embodiments, the HCAb with antigen-binding specificity for PDGF-BB comprises CDRs of SEQ ID NOs:31-33. In some embodiments, the HCAb with antigen-binding specificity for PDGF-BB comprises CDRs of SEQ ID NOs:35-37. In some embodiments, the HCAb with antigen-binding specificity for PDGF-BB comprises CDRs of SEQ ID NOs:39-41. In some embodiments, the HCAb with antigen-binding specificity for PDGF-BB comprises CDRs of SEQ ID NOs:43-45. In some embodiments, the HCAb with antigen-binding specificity for PDGF-BB comprises CDRs of SEQ ID NOs: 47-49. In some embodiments, the HCAb with antigen-binding specificity for PDGF-BB comprises CDRs of SEQ ID NOs:51-53.

In some embodiments, at least one amino acid of the HCAb VH region sequence is substituted, added, or deleted and the HCAb retains its specificity for PDGF.

Also disclosed herein are HCAb with antigen-binding specificity for PDGF-BB, wherein the CDR1 comprises GFTFSSY (SEQ ID NO:23), and wherein the amino acid at position 7 is substituted with any amino acid and the HCAb retains its specificity for PDGF-BB. In other embodiments, the amino acid at position 7 is substituted with a conservative amino acid and the HCAb retains its specificity for PDGF-BB. In yet other embodiments, the amino acid at position 7 is substituted with an amino acid of the same class and the HCAb retains its specificity for PDGF-BB.

Also disclosed herein are HCAb with antigen-binding specificity for PDGF, wherein the CDR2 comprises ISGSGGST (SEQ ID NO:24) and wherein one or more of the amino acids at positions 3 or 8 are substituted with any amino acid and the HCAb retains its specificity for PDGF-BB. In other embodiments, one or more of the amino acids at positions 3 or 8 are substituted with a conservative amino acid and the HCAb retains its specificity for PDGF-BB. In yet other embodiments, one or more of the amino acids at positions 3 or 8 are substituted with an amino acid of the same class and the HCAb retains its specificity for PDGF-BB.

Also disclosed herein are HCAb with antigen-binding specificity for PDGF, wherein the CDR3 comprises RNSEIFMVKGVIQYNS (SEQ ID NO:25), and wherein one or more of the amino acids at positions 3, 4, 8, 9, 10, 11, 12, 13, 14, or 16 are substituted with any amino acid and the HCAb retains its specificity for PDGF-BB. In other embodiments, one or more of the amino acids at positions 3, 4, 8, 9, 10, 11, 12, 13, 14, or 16 are substituted with a conservative amino acid and the HCAb retains its specificity for PDGF-BB. In yet other embodiments, one or more of the amino acids at positions 3, 4, 8, 9, 10, 11, 12, 13, 14, or 16 are substituted with an amino acid of the same class and the HCAb retains its specificity for PDGF-BB.

Also disclosed herein are human or humanized antibodies which compete for binding to PDGF-BB with HCAb P36F3, P36E10, P36E8, P36C12, P36A4, P36A3, P36D9, P36E4, P36E9, P36G9, and/or P36H4.

In certain embodiments, bispecific antibodies having a first antigen-binding specificity to PDGF and a second antigen-binding specificity to VEGF are provided. In other embodiments, a first antigen-binding specificity is represented by HCAb P36F3 P36E10, P36E8, P36C12, P36A4, P36A3, P36D9, P36E4, P36E9, P36G9, and/or P36H4, or a VH domain thereof. In yet other embodiments, a second antigen-binding specificity is represented by bevacizumab, or a VH or VL region thereof. In certain embodiments, a second antigen-binding specificity is represented by ranibizumab, or a VH or VL region thereof.

Also disclosed are bispecific antibodies having a first antigen-binding specificity to PDGF and a second antigen-binding specificity to ANG-2. In certain embodiments, a first antigen-binding specificity is represented by HCAb P36F3, P36E10, P36E8, P36C12, P36A4, P36A3, P36D9, P36E4, P36E9, P36G9, and/or P36H4, or a VH domain thereof. In other embodiments, a second antigen-binding specificity is represented by HCAb A33A8 (SEQ ID NO:54), A1G2 (SEQ ID NO:55), A1F8 (SEQ ID NO:56), A2B6 (SEQ ID NO:57), or A1B1 (SEQ ID NO:58), or an antibody comprising at least one CDR thereof.

Also disclosed herein are methods of treating ophthalmologic disorders comprising administering to a subject in need thereof, a PDGF-binding HCAb having a VH region disclosed herein, or a bispecific antibody disclosed herein.

Also disclosed herein is the use of a PDGF-binding HCAb having a VH region disclosed herein, or a bispecific antibody disclosed herein in the manufacture of a medicament for treating an ophthalmologic disorder in a subject in need thereof.

In some embodiments, the ophthalmologic disorder is selected from the group consisting of dry (non-exudative) age-related macular degeneration, wet (exudative or neovascular) age-related macular degeneration, choroidal neovascularization (CNV), cystoid macula edema (CME), myopia-associated choroidal neovascularization, vascular streaks, diabetic macular edema (DME), macular edema, retinal vein occlusion, abnormal corneal angiogenesis, pterygium conjunctivae, subretinal edema, or intraretinal edema. In some embodiments, the abnormal corneal angiogenesis is as a result of keratitis, corneal transplantation, keratoplasty or hypoxia.

DETAILED DESCRIPTION

Figure 1A:
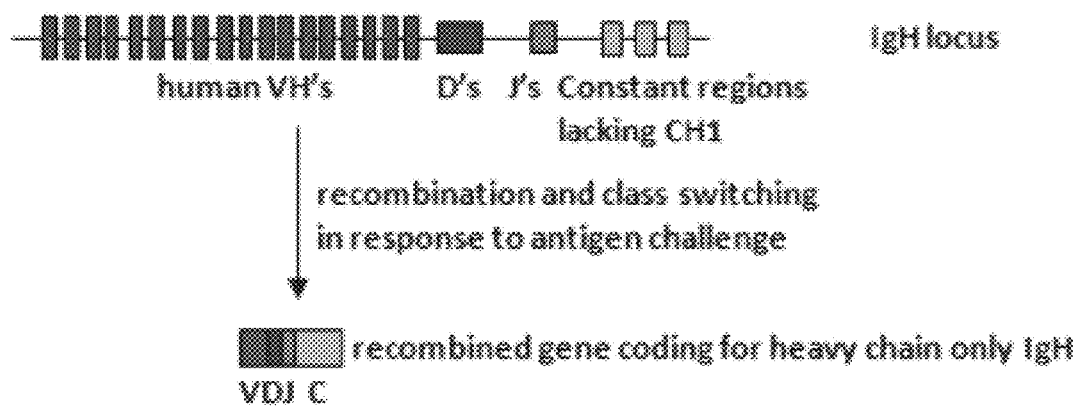
FIG. 1A depicts the human immunoglobulin locus in the HCAb transgenic mouse (Harbour Antibodies).

Disclosed herein are monospecific heavy chain only antibodies (HCAb) having specificity for PDGF and bispecific antibodies having specificity for PDGF and ANG-2, or for PDGF and VEGF.

PDGF plays a significant role in blood vessel formation (angiogenesis), the growth of blood vessels from already-existing blood vessel tissue. PDGF is a potent mitogen for cells of mesenchymal origin, including fibroblasts, smooth muscle cells and glial cells. PDGF is a dimeric glycoprotein comprised of two A (-AA) or two B (-BB) subunits, or a combination of the two (-AB). The subunit is a 211 amino acid sequence (UniProtKB—P04085; SEQ ID NO:1 MRT-LACLLLLGCGYLAHVLAEEAEIPREVIERLARSQIHS-IRDLQRLLEIDSVGSEDSLDTSLRAH GVHATKHVPEK RPLPIRRKRSIEEAVPAVCKTRTVIYEIPRSQVDPTSA N FLIWPPCVEVKRCTG CCNTSSVKCQPSRVHHRSVK V AKVEYVRKKPKLKEVQVRLEEHLECACATTSLNPD YREEDT GRPRESGKKRKRKRLKPT) and the B subunit is a 241 amino acid sequence (UniProtKB—P01127, SEQ ID NO:2 MNRCWALFLSLCCYLRLVSAEGDPIPEELY-EMLSDHSIRSFDDLQRL LHGDPGEEDGAELDLNMT RSHSGGELESLARGRRSLGSLTIAEPAMIAECKTRTE-VFEISRRLI DRTNANFLVWPPCVEVQRCSGCCNNRN-VQCRPTQVQLRPVQVRKIEIVRKKPIFKKATVTLED H LACKCETVAAARPVTRSPGGSQEQRAKTPQTR VT IR TVRVRRPPKGKHRKFKHTHDKTALKE TLGA). Thus, in various embodiments, an antibody is disclosed having specificity for PDGF-AA, PDGF-BB, and/or PDGF-AB, or a fragment thereof. In both mouse and human, the PDGF signaling network consists of four ligands, PDGFA-D, and two receptors, PDGFRalpha and PDGFRbeta (receptor tyrosine kinases). All PDGFs function as secreted, disulfide-linked homodimers, but only PDGFA and B can form functional heterodimers.

Thus, in certain embodiments, the PDGF is PDGF-AA, PDGF-BB, or PDGF-AB.

Thus, disclosed herein are monospecific and bispecific HCAb antibodies to PDGF and methods of treating ophthalmological disorders using the disclosed antibodies.

Antibodies for treatment of diseases are well known in the art. As used herein, the term "antibody" refers to a monomeric or multimeric protein comprising one or more polypeptide chains that comprise antigen-binding sites. An antibody binds specifically to an antigen and may be able to modulate the biological activity of the antigen. As used herein, the term "antibody" can include "full length antibody" and "antibody fragments." The terms "binding site" or "antigen-binding site" as used herein denotes the region(s) of an antibody molecule to which a ligand actually binds. The term "antigen-binding site" comprises an antibody heavy chain variable domain (VH) and an antibody light chain variable domain (VL).

Antibody specificity refers to selective recognition of the antibody for a particular epitope of an antigen. Natural antibodies, for example, are monospecific. The term "monospecific" antibody as used herein denotes an antibody that has one or more binding sites each of which bind to the same epitope of the same antigen. The monovalent, monospecific antibodies disclosed herein are specific for PDGF.

"Bispecific antibodies" refers to antibodies which have two different antigen-binding specificities. Bispecific antibodies disclosed herein are specific for PDGF and VEGF or ANG-2.

The term "valent" as used herein denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies disclosed herein are "bivalent." However, monospecific bivalent antibodies are within the scope of the present disclosure in which the two antigen-binding sites bind the same antigen. The antigen-binding sites of monospecific bivalent antibodies can bind either the same epitope or different epitopes on the antigen.

By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1, CH2, and CH3. In some mammals, for example in camels and llamas, IgG antibodies consist of only two heavy chains (HCAb), each heavy chain comprising a variable domain attached to the Fc region (CH2 and CH3 domains).

Natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Each of the light and heavy chains are made up of two distinct regions, referred to as the variable and constant regions. For the IgG class of immunoglobulins, the heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively. The constant regions show less sequence diversity, and are responsible for binding a number of natural proteins to elicit important biochemical events.

The variable region of an antibody contains the antigen binding determinants of the molecule, and thus determines the specificity of an antibody for its target antigen. The variable region is so named because it is the most distinct in sequence from other antibodies within the same class. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are six CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens.

The genes encoding the immunoglobulin locus comprise multiple V region sequences along with shorter nucleotide sequences named "D" and "J" and it is the combination of the V, D, and J nucleotide sequence that give rise to the VH diversity.

Antibodies are grouped into classes, also referred to as isotypes, as determined genetically by the constant region. Human constant light chains are classified as kappa (Cκ) and lambda (Cλ) light chains. Heavy chains are classified as mu (μ), delta (δ), gamma (γ), alpha (α), or epsilon (ε), and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The disclosed HCAb antibodies and bispecific antibodies can have constant regions comprising all, or part, of the above-described isotypes.

Also within the scope of the present disclosure are antibody fragments including, but are not limited to, (i) a Fab fragment comprising VL, CL, VH, and CH1 domains, (ii) a Fd fragment comprising VH and CH1 domains, (iii) a Fv fragment comprising VL and VH domains of a single antibody; (iv) a dAb fragment comprising a single variable region, (v) isolated CDR regions, (vi) F(ab')$_2$ fragment, a bivalent fragment comprising two linked Fab fragments, and (vii) a single chain Fv molecule (scFv), wherein a VH domain and a VL domain are linked by a peptide linker which allows the two domains to associate to form an antigen binding site. In certain embodiments, antibodies are produced by recombinant DNA techniques. In additional embodiments, antibodies are produced by enzymatic or chemical cleavage of naturally occurring antibodies.

By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor." In certain embodiments, humanization relies principally on the grafting of donor CDRs onto acceptor (human) VL and VH frameworks. This strategy is referred to as "CDR grafting." "Backmutation" of selected acceptor framework residues to the corresponding donor residues is often required to regain affinity that is lost in the initial grafted construct. The humanized antibody optimally also will comprise at least a portion of an immunoglobulin constant region, typically that of a human immunoglobulin, and thus will typically comprise a human Fc region. Humanization or other methods of reducing the immunogenicity of nonhuman antibody variable regions may include resurfacing methods. In one embodiment, selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Pat. No. 6,797,492, incorporated by reference herein for all it discloses regarding CDR grafting. Structure-based methods may be employed for humanization and affinity maturation, for example as described in U.S. Pat. No. 7,117,096, incorporated by reference herein for all it discloses regarding humanization and affinity maturation.

In various embodiments herein, the antibodies are heavy chain only antibodies (HCAb). Camelids (camels, dromedary, and llamas) contain, in addition to normal heavy and light chain antibodies (2 light chains and 2 heavy chains in one antibody), single chain antibodies (containing only heavy chains) (see FIG. 1B). These are coded for by a distinct set of VH segments referred to as VHH genes. The VH and VHH are interspersed in the genome (i.e., they appear mixed in between each other). The identification of an identical D segment in a VH and VHH cDNA suggests the common use of the D segment for VH and VHH. Natural VHH-containing antibodies are missing the entire CH1 domain of the constant region of the heavy chain. The exon coding for the CH1 domain is present in the genome but is spliced out due to the loss of a functional splice acceptor sequence at the 5' side of the CH1 exon. As a result the VDJ region is spliced onto the CH2 exon. When a VHH is recombined onto such constant regions (CH2, CH3) an antibody is produced that acts as a single chain antibody (i.e., an antibody of two heavy chains without a light chain interaction). Binding of an antigen is different from that seen with a conventional antibody, but high affinity is achieved the same way, i.e., through hypermutation of the variable region and selection of the cells expressing such high affinity antibodies.

Figure 1B:
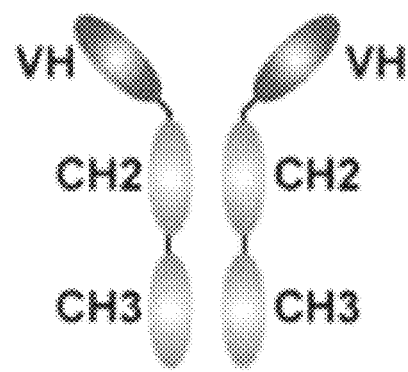
FIG. 1B depicts the HCAb antibody structure produced by the HCAb mouse.

In an exemplary embodiment, the disclosed HCAb are produced by immunizing a transgenic mouse in which endogenous murine antibody expression has been eliminated and human transgenes have been introduced (see FIG. 1A). HCAb mice are disclosed in U.S. Pat. Nos. 8,883,150, 8,921,524, 8,921,522, 8,507,748, 8,502,014, US 2014/0356908, US2014/0033335, US2014/0037616, US2014/0356908, US2013/0344057, US2013/0323235, US2011/0118444, and US2009/0307787, all of which are incorporated herein by reference for all they disclose regarding heavy chain only antibodies and their production in transgenic mice. The HCAb mice are immunized and the resulting primed spleen cells fused with a murine myeloma cells to form hybridomas. The resultant HCAb can then be made fully human by replacing the murine CH2 and CH3 regions with human sequences.

Figure 2A:
FIG. 2A-E depicts several forms of bispecific antibodies including single domain VH (FIG. 2A); bi-specific HCAb antibodies (FIGS. 2B and 2C); tetrameric antibody/VH bispecific antibodies (FIG. 2D); bispecific Fab/VH antibodies (FIG. 2E). The second antigen-binding domain is depicted as an oval. Optional locations for the second antigen-binding domain are indicated by asterisks.
Figure 2B:
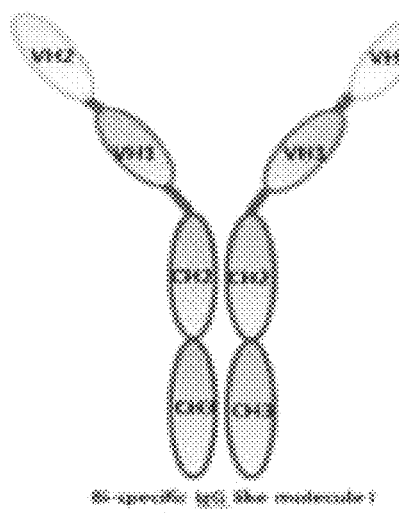
Figure 2C:
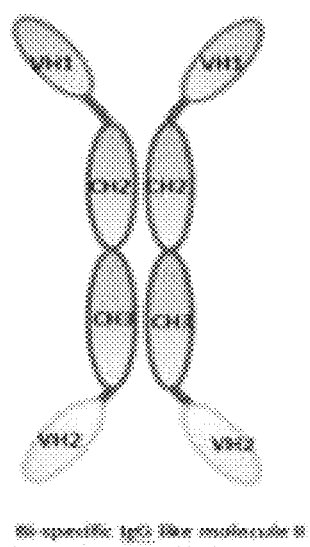
Figure 2D:
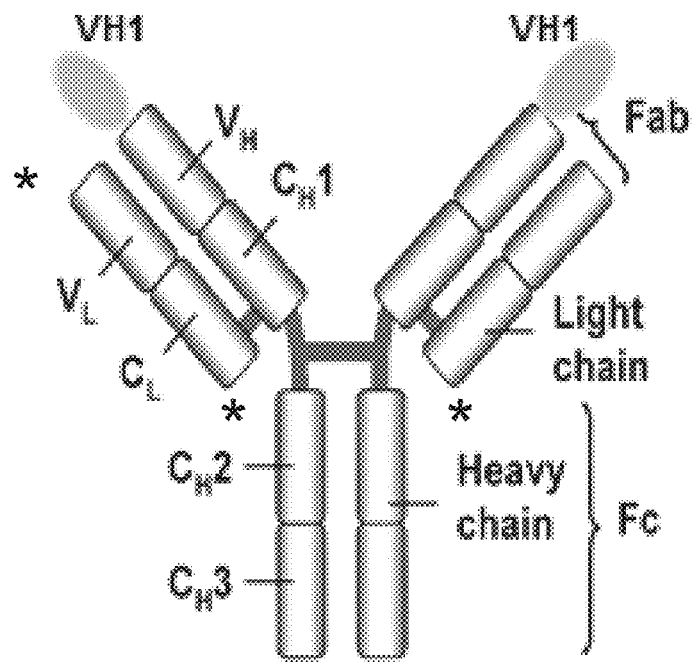
Figure 2E:
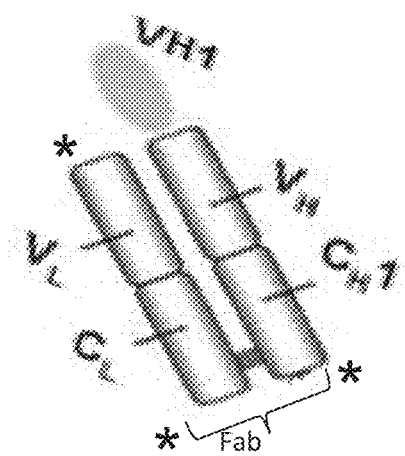

Also disclosed herein are bifunctional antibodies in which two antigen binding domains are joined in a single bispecific molecule. Bifunctional antibodies can take many forms including (i) bi-specific Fv fragments (FIG. 2A); (ii) HCAb of a first specificity having associated therewith a second VH domain having a second specificity (FIGS. 2B and 2C); (iii) tetrameric monoclonal antibodies with a first specificity having associated therewith with a second VH domain having a second specificity, wherein the second VH domain is associated with a first VH domain (FIG. 2D); and (iv) Fab fragments (VH-CH1/VL/CL) of a first specificity having associated therewith a second VH domain with a second specificity (FIG. 2E-2F). Exemplary Fab fragments are depicted in FIG. 2E in which the second VH sequence having the second specificity is associated with the C-terminus or the N-terminus of the first VH domain, or the C-terminus or the N-terminus of the first CH1 or first CL domains. In additional embodiments also depicted in FIG. 2E, VH sequences having a second and/or a third specificity can be associated with the C-terminus or the N-terminus of the first VH domain, or the C-terminus or the N-terminus of the first CH1 or first CL domains.

Bispecific antibodies may include linker sequences linking a sequence of an PDGF-binding antibody, such as P36F3, P36E10, P36E8, P36C12, P36A4, P36A3, P36D9, P36E4, P36E9, P36G9, or P36H4, to a VH region with a second specificity which allows for proper folding of the sequences to generate the desired three-dimensional conformation and antigen binding profiles. Suitable linkers include, but are not limited to, EPKSCD (SEQ ID NO:3), ASTKGP (SEQ ID NO:4), and (GGGGS)$_n$ (SEQ ID NO:5), wherein n is an integer between 0 and 8. In one embodiment, n is 1.

The bispecific antibodies disclosed herein are bivalent comprising a first specificity to PDGF, and a second specificity can include, but is not limited to, a vascular endothelial growth factor (VEGF) and angiopoietin 2 (ANG-2). Within the scope of the present disclosure are bispecific antibodies wherein the first specificity and the second specificity are independently ANG-2, VEGF, or PDGF, with the only limitation that the first and second specificity cannot be the same.

The VEGF family in mammals is comprised of five members: VEFG-A, placenta growth factor (PGF), VEGF-B, VEGF-C, and VEGF-D. All members of the VEGF family stimulate cellular responses by binding to tyrosine kinase receptors (the VEGFRs) on the cell surface, causing them to dimerize and become activated through transphosphorylation, although to different sites, times, and extents. The VEGF receptors have an extracellular portion consisting of 7 immunoglobulin-like domains, a single transmembrane spanning region, and an intracellular portion containing a split tyrosine-kinase domain. VEGF-A binds to VEGFR-1 (Flt-1) and VEGFR-2 (KDR/Flk-1). VEGFR-2 appears to mediate almost all of the known cellular responses to VEGF. The function of VEGFR-1 is less well-defined, although it is thought to modulate VEGFR-2 signaling. Another function of VEGFR-1 may be to act as a dummy/decoy receptor, sequestering VEGF from VEGFR-2 binding (this appears to be particularly important during vasculogenesis in the embryo). VEGF-C and VEGF-D, but not VEGF-A, are ligands for a third receptor (VEGFR-3/Flt4), which mediates lymphangiogenesis. The receptor (VEGFR-3) is the site of binding of main ligands (VEGF-C and VEGF-D), which mediates perpetual action and function of ligands on target cells. VEGF-C stimulate lymphangiogenesis (via VEGFR-3) and angiogenesis via VEGFR-2. VEGF-A is a 232 amino acid sequence (UniProtKB—P15692).

Human angiopoietins-1 and -2 (ANG-1 and ANG-2 (UniProtKB—O15123; alternatively abbreviated with ANGPT2 or ANG2)) were discovered as ligands for Ties, a family of tyrosine kinases that is selectively expressed within the vascular endothelium. There are four definitive members of the angiopoietin family. Angiopoietin-3 and -4 (ANG-3 and ANG-4) may represent widely diverged counterparts of the same gene locus in mouse and man. ANG-1 and ANG-2 were originally identified in tissue culture experiments as agonist and antagonist, respectively. All of the known angiopoietins bind primarily to Tie-2. ANG-1 supports endothelial cell (EC) survival and to promote endothelium integrity, whereas ANG-2 had the opposite effect and promoted blood vessel destabilization and regression in the absence of the survival factors VEGF or basic fibroblast growth factor. However, many studies of ANG-2 function have suggested a more complex situation. ANG-2 might be a complex regulator of vascular remodeling that plays a role in both vessel sprouting and vessel regression. Supporting such roles for ANG-2, expression analysis reveals that ANG-2 is rapidly induced, together with VEGF, in adult settings of angiogenic sprouting, whereas ANG-2 is induced in the absence of VEGF in settings of vascular regression. Consistent with a context-dependent role, ANG-2 specifically binds to the same endothelial-specific receptor, Tie-2, which is activated by ANG-1, but has context-dependent effects on its activation.

ANG-1 and ANG-2 have similar effects in corneal angiogenesis assays, acting synergistically with VEGF to promote growth of new blood vessels. At high concentration, ANG-2 acts as an apoptosis survival factor for endothelial cells during serum deprivation apoptosis through activation of Tie-2 via PI-3 Kinase and Akt pathway.

The role of ANG-1 is thought to be conserved in the adult, where it is expressed widely and constitutively. In contrast, ANG-2 expression is primarily limited to sites of vascular remodeling where it is thought to block the constitutive stabilizing or maturing function of ANG-1, allowing vessels to revert to, and remain in, a plastic state which may be more responsive to sprouting signals.

ANG-2 is expressed during development at sites where blood vessel remodeling is occurring. In adult individuals, ANG-2 expression is restricted to sites of vascular remodeling as well as in highly vascularized tumors. ANG-2 is required for postnatal angiogenesis. Developmentally programmed regression of the hyaloid vasculature in the eye does not occur in ANG-2 knockout mice and their retinal blood vessels fail to sprout out from the central retinal artery. Deletion of ANG-2 results in profound defects in the patterning and function of the lymphatic vasculature. Genetic rescue with ANG-1 corrects the lymphatic, but not the angiogenesis defects.

Thus, disclosed herein are HCAb specific for PDGF and bispecific antibodies specific for both ANG-2 and PDGF or specific for both PDGF and VEGF. In other embodiments, the PDGF/VEGF bispecific antibody is a bispecific antibody formed from the human anti-PDGF-BB HCAb antibody P36F3 disclosed herein and the VH and/or VL regions of any human or humanized VEGF-specific antibody. VEGF-specific antibodies can include, but are not limited to the antibodies disclosed in U.S. Pat. Nos. 7,297,334, 6,884, 8798,945,552, WO1998045331, US20150175689, and US20090142343. Exemplary humanized anti-VEGF antibodies are bevacizumab and ranibizumab.

In certain embodiments, the PDGF/VEGF bispecific antibody is a bispecific antibody formed from the human anti-PDGF-BB HCAb antibody P36F3 disclosed herein and the VH and/or VL region of bevacizumab (AVASTIN®, Genentech). The amino acid sequence of bevacizumab is disclosed in U.S. Pat. No. 7,297,334 which is incorporated by reference herein for all it discloses regarding the amino acid sequence of anti-VEGF antibodies. In certain embodiments, the VH sequence of bevacizumab is EVQLVES-GGGLVQPGGSLRLSCAASGYTFTNYGMNW VR QA P GKGLEWVGWINTYTGEPTYAADFKRRFTFSLDTSK-STAYLQMNSLRAEDTAVYYCAK YPHYYGSSHWY FD VWGQGTLVTVSS (SEQ ID NO:6) and the VL sequence of bevacizumab is DIQMTQSPSSLSASVGDRVTITCSAS Q DISNYLNWYQQKPGKAPKVLIYFTSSLHSGVPS RF S GSGSGTDFTLTISSLQPEDFATYYCQQYSTVPWTFG Q GTKVEIKR (SEQ ID NO:7).

In certain embodiments, the PDGF/VEGF bispecific antibody is a bispecific antibody formed from the human anti-PDGF-BB HCAb antibody P36F3 disclosed herein and the VH and/or VL regions of ranibizumab (LUCENTIS®, Genentech). The amino acid sequence of ranibizumab is disclosed in U.S. Pat. No. 6,884,879 which is incorporated by reference herein for all it discloses regarding the amino acid sequence of anti-VEGF antibodies. In certain embodiments, the VH sequence of ranibizumab is EVQLVES-GGGLVQPGGSLRLSCAASGYDF THYGMNWVRQ AP GKGLEWVGWINTYTGEPTYAADFKRRFTFSLDTSK-STAYLQMNSLRAEDT AVYYCAKYPYYYGTSHWY F DVWGQGTLVTVSS (SEQ ID NO:8) and the VL sequence of ranibizumab is DIQLTQSPSSLSASVGDRVTITCSA SQDISNYLNWYQQKPGKAPKVLIYFTSSL HSGV PS R FSGSGSGTDFTLTISSLQPEDFATYYCQQYSTVPWTF-GQGTKVEIKR (SEQ ID NO:9).

In other embodiments, the PDGF/ANG-2 bispecific antibody is a bispecific antibody formed from the human anti-PDGF-BB HCAb antibody P36F3 disclosed herein and the VH and/or VL regions of any human or humanized ANG-2-specific antibody. Exemplary humanized anti-ANG-2 antibodies are disclosed in, for example, US2010/0159587 and US20130259868, which are incorporated by reference herein for all they disclose regarding anti-ANG-2 antibodies. Exemplary ANG-2-binding antibodies are also disclosed in co-pending application PCT/US2016/044838 filed on Jul. 29, 2016 and having attorney docket number 19864NTB), which is incorporated by reference for all it discloses regarding ANG-2-binding antibodies.

Also within the scope of the present disclosure are amino acid sequence variants of the human anti-PDGF monospecific or bispecific antibodies are prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletion, insertion, and substitution is made to arrive at the final construct, provided that the final construct possesses the desired characteristics. The amino acid changes also may alter post-translational processes of the humanized or variant antibodies, such as changing the number or position of glycosylation sites.

A useful method for identification of certain residues or regions of the antibodies that are preferred locations for mutagenesis is called "alanine scanning mutagenesis." A residue or group of target residues are identified (e.g., charged residues such as Arg, Asp, His, Lys, and Glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-PDGF antibody with an N-terminal methionyl residue or the antibody fused to an epitope tag. Other insertional variants of the antibody molecules include the fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Hydrophobic: Norleucine, Met, Ala, Val, Leu, Ile;
(2) Neutral hydrophilic: Cys, Ser, Thr;
(3) Acidic: Asp, Glu;
(4) Basic: Asn, Gin, His, Lys, Arg;
(5) Residues that influence chain orientation: Gly, Pro; and
(6) Aromatic: Trp, Tyr, Phe.

Non-conservative substitutions will entail exchanging a member of one of these classes for another class.

Any cysteine residue not involved in maintaining the proper conformation of the monospecific or bispecific anti-PDGF antibodies also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene IIII product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human PDGF. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the monospecific or bispecific anti-PDGF antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an anti-PDGF antibody.

Other modifications of the monospecific or bispecific anti-PDGF antibodies are contemplated. For example, it may be desirable to modify the antibodies with respect to effector function, so as to enhance the effectiveness of the antibody in treating disease, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Homodimeric antibodies with enhanced anti-tumor activity may also be prepared using heterobifunctional cross-linkers. Alternatively, an antibody can be engineered which has dual Fc regions and may thereby have enhanced complement lysis and ADCC capabilities.

Also within the scope of the present disclosure are anti-PDGF HCAb having at least 85% identity, at least 90% identity, at least 93% identity, at least 96% identity, or at least 98% identity to sequence of an anti-PDGF HCAb disclosed herein.

Exemplary variants, or mutated anti-PDGF HCAb comprise one or more of the sequences of SEQ ID Nos: 10, 14, 18, 22, 26, 30, 34, 38, 42, 46, or 50. or one or more of the CDRs selected from SEQ ID NOs: 11-13, 15-17, 19-21, 23-25, 27-29, 31-33, 35-37, 39-41, 43-45, 47-49 and 51-53, wherein one or more amino acids are substituted with an amino acid according to Table 1. In some embodiments, up to 1, up to 2, up to 3, up to 4, up to 5, up to 6, up to 7, up to 8, up to 9, up to 10, up to 12, up to 14, up to 16, up to 18, or up to 20 amino acids are added, substituted, or deleted with the proviso that the substituted sequence retains the binding specificity, or has an increased binding specificity, of the un-substituted sequence. In other embodiments, up to 1, up to 2, up to 3, up to 4, up to 5, up to 6, up to 7, up to 8, up to 9, up to 10, up to 12, up to 14, up to 16, up to 18, or up to 20 amino acids are added, substituted, or deleted with the proviso that the substituted sequence retains at least 85% identity, at least 90% identity, at least 93% identity, at least 96% identity, or at least 98% identity to entire length of the un-substituted sequence.

In certain embodiments, the variant, or mutated anti-PDGF HCAb includes one or more additions, substitutions, or deletions in the variable region. In some embodiments, the variant, or mutated anti-PDGF HCAb includes one or more additions, substitutions, or deletions in one or more complementarity determining regions. In some embodiments, the variant, or mutated anti-PDGF HCAb includes one or more additions, substitutions, or deletions in one or more framework region. In yet more embodiments, the variant, or mutated anti-PDGF HCAb includes one or more additions, substitutions, or deletions in one or more constant regions.

In certain embodiments, the variant, or mutated anti-PDGF HCAb includes one or more additions, substitutions, or deletions in CDR1. In some embodiments, the variant, or mutated anti-PDGF HCAb includes one or more additions, substitutions, or deletions in CDR2. In some embodiments, the variant, or mutated anti-PDGF HCAb includes one or more additions, substitutions, or deletions in CDR3.

In certain embodiments, the variant, or mutated anti-PDGF HCAb includes one or more additions, substitutions, or deletions in the framework 1 region. In some embodiments, the variant, or mutated anti-PDGF HCAb includes one or more additions, substitutions, or deletions in the framework 2 region. In some embodiments, the variant, or mutated anti-PDGF HCAb includes one or more additions, substitutions, or deletions in the framework 3 region. In some embodiments, the variant, or mutated anti-PDGF HCAb includes one or more additions, substitutions, or deletions in the framework 4 region. In some embodiments, the variant, or mutated anti-PDGF HCAb includes one or more additions, substitutions, or deletions in the hinge region.

Also disclosed herein are immunoconjugates comprising the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate).

Chemotherapeutic agents useful in the generation of such immunoconjugates have been described. Enzymatically active toxins and fragments thereof which can be used include diphtheria A chain, nonbinding active fragments of diphtheria toxin, exotoxin A chain (from *Pseudomonas aeruginosa*), ricin A chain, botulinum toxins, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *saponaria officinalis* inhibitor, gelonin, mitogillin, restrictocin, phenomycin, enomycin and the tricothecenes. A variety of radionuclides are available for the production of radioconjugated monospecific or bispecific anti-PDGF antibodies. Examples include $^{212}$Bi, $^{131}$I, $^{131}$In, $^{90}$Y, and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of radionucleotide to an antibody.

In another embodiment, an antibody may be conjugated to a "receptor" (such streptavidin) for utilization in pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionuclide).

The monospecific or bispecific anti-PDGF antibodies disclosed herein may also be formulated in liposomes. Liposomes containing the antibody are prepared by methods known in the art, such as described in U.S. Pat. Nos. 4,485,045, 4,544,545, and U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibodies can be conjugated to the liposomes via a disulfide interchange reaction.

Covalent modifications of the monospecific or bispecific anti-PDGF antibodies are also included within the scope of this disclosure. They may be made by chemical synthesis or by enzymatic or chemical cleavage of the antibody, if applicable. Other types of covalent modifications of the antibodies are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference for all it discloses regarding covalent modifications of polypeptides. An exemplary type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835, 4,496,689, 4,301,144, 4,670,417, 4,791,192, or U.S. Pat. No. 4,179,337.

The monospecific and bispecific antibodies disclosed herein may be produced by recombinant means. Thus, disclosed herein are nucleic acids encoding the antibodies, expression vectors containing nucleic acids encoding the antibodies, and cells comprising the nucleic acid encoding the antibodies. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the antibody sequences are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis).

Accordingly certain embodiments disclosed herein include a method for the preparation of a monospecific or bispecific antibody, comprising the steps of a) transforming a host cell with at least one expression vector comprising nucleic acid molecules encoding the antibody; b) culturing the host cell under conditions that allow synthesis of the antibody molecule; and c) recovering said antibody molecule from the culture.

The antibodies are suitably separated from the culture medium by conventional immunoglobulin purification procedures such as, for example, protein A-Sepharose, hydroxylapatite chromatography, gel electrophoresis, dialysis, or affinity chromatography.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection can be carried out e.g. by the calcium phosphate precipitation method. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The term "host cell" as used herein denotes any kind of cellular system which can be engineered to generate the antibodies disclosed herein. In one embodiment HEK293 cells and CHO cells are used as host cells.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Also disclosed herein are isolated nucleic acid encoding the monospecific or bispecific human anti-PDGF antibodies, vectors and host cells comprising the nucleic acids, and recombinant techniques for the production of the antibodies.

For recombinant production of the antibodies, the nucleic acid encoding it may be isolated and inserted into a replicable vector for further cloning (amplification of the DNA) or for expression. In some embodiments, the antibody may be produced by homologous recombination, e.g. as described in U.S. Pat. No. 5,204,244, specifically incorporated herein by reference for all it discloses regarding antibody production. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615, specifically incorporated herein by reference for all it discloses regarding protein expression.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *S. marcescens*, and *Shigella*, as well as Bacilli such as *B. subtilis* and *B. licheniformis*, *Pseudomonas* such as *P. aeruginosa*, and *Streptomyces*. One exemplary *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for monospecific or bispecific human anti-PDGF antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *Yarrowia* (EP 402,226); *Pichia pastoris* (EP 183,070); *Candida*; *Trichoderma reesei* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated monospecific or bispecific human anti-PDGF antibodies are derived from multicellular organisms, including invertebrate cells such as plant and insect cells. Numerous baculoviral strains and variants and corresponding permissive insect host cells from hosts such as *Spodoptera frugiperda* (caterpillar), *Aedes aegypti* (mosquito), *A. albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *S. frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and human hepatoma cells (Hep G2).

Host cells are transformed with the above-described expression vectors for monospecific or bispecific anti-PDGF antibody production and cultured in conventional nutrient media modified as appropriate for inducing promoters, selecting transformants, or amplifying the genes encoding the desired sequences.

The host cells used to produce the monospecific or bispecific human anti-PDGF antibodies may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, U.S. Pat. Nos. 4,767,704; 4,657,866; 4,927,762; 4,560,655; or U.S. Pat. No. 5,122, 469; WO 90/03430; WO 87/00195; or US Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMICIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains. Protein G is recommended for all mouse isotypes and for human γ3. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Also disclosed herein are methods of using the monospecific and bispecific human anti-PDGF antibodies for the treatment of ophthalmological disorders. Examples of ophthalmological disorders include, but are not limited to, dry (non-exudative) age-related macular degeneration, wet (exudative or neovascular) age-related macular degeneration, choroidal neovascularization (CNV), cystoid macula edema (CM E), myopia-associated choroidal neovascularization, vascular streaks, diabetic macular edema (DME), macular edema, macular edema due to retinal vein occlusion, and angiogenesis in the front of the eye like corneal angiogenesis following e.g. keratitis, corneal transplantation or keratoplasty, corneal angiogenesis due to hypoxia (extensive contact lens wearing), pterygium conjunctivae, subretinal edema and intraretinal edema. Examples of age-related macular degeneration (AMD) include but are not limited to dry or nonexudative AMD, or wet or exudative or neovascular AMD.

Macular degeneration, also referred to as age-related macular degeneration, is the most common cause of vision loss in the United States in those 50 or older, and its prevalence increases with age. AMD is classified as either wet (neovascular) or dry (non-neovascular). The dry form of the disease is most common. It occurs when the central retina has become distorted, pigmented, or most commonly, thinned, a process associated with atrophy of the retinal pigment epithelium and loss of macular photoreceptors. The result is central geographic atrophy. The wet form of the disease is responsible for most severe loss of vision. The wet form is usually associated with aging, but other diseases that can cause wet macular degeneration include severe myopia and some intraocular infections such as histoplasmosis, which may be exacerbated in individuals with AIDS. The wet form is characterized by abnormal blood vessels growing through the retinal pigment epithelium, resulting in hemorrhage, exudation, scarring, or retinal detachment.

Disclosed herein are sustained release formulations of monospecific and bispecific human anti-PDGF antibodies for treatment of ocular disorders. Thus, the monospecific and bispecific human anti-PDGF antibodies, can be released into the vitreous over a 3 to 6 month period from a sustained release drug delivery system to provide long term treatment of a chronic ocular condition such as dry AMD.

A hydrogel is a colloidal gel formed as a dispersion in water or other aqueous medium. Thus a hydrogel is formed upon formation of a colloid in which a dispersed phase (the polymer) has combined with a continuous phase (i.e., water) to produce a viscous jellylike product; for example, coagulated silicic acid. A hydrogel is a three-dimensional network of hydrophilic polymer chains that are crosslinked through either chemical or physical bonding. Because of the hydrophilic nature of the polymer chains, hydrogels absorb water and swell (unless they have already absorbed their maximum amount of water). The swelling process is the same as the dissolution of non-crosslinked hydrophilic polymers. By definition, water constitutes at least 10% of the total weight (or volume) of a hydrogel.

Examples of hydrogels include synthetic polymers such as polyhydroxy ethyl methacrylate, and chemically or physically crosslinked polyvinyl alcohol, polyacrylamide, poly (N-vinyl pyrrolidone), polyethylene oxide, and hydrolysed polyacrylonitrile. Examples of hydrogels which are organic polymers include covalent or ionically crosslinked polysaccharide-based hydrogels such as the polyvalent metal salts of alginate, pectin, carboxymethyl cellulose, heparin, hyaluronate and hydrogels from chitin, chitosan, pullulan, gellan and xanthan. The particular hydrogels used in our experiment were a cellulose compound (i.e., hydroxypropylmethylcellulose [HPMC]) and a high molecular weight hyaluronic acid (HA).

In some embodiments, a hydrogel formulation for intravitreal injection is disclosed using a polymeric hyaluronic acid and the monospecific and/or bispecific human anti-PDGF antibodies disclosed herein. This drug delivery system can provide sustained-release of a low daily dose of the monospecific and bispecific human anti-PDGF antibodies over a 3 to 6 month period and prevent of conversion from dry to wet AMD. The drug delivery system can also comprise microsphere encapsulation of the monospecific and bispecific human anti-PDGF antibody in the hydrogel. The sustained-release drug delivery system can provide the necessary anti-PDGF blockade in eye to reduce the chance of progression from dry to neovascular AMD. In addition, the low doses released in the eye over a prolonged period of time do not provide a systemic toxic level of the agent.

The sustained release drug delivery system can also be used to provide a sustained-release anti-PDGF blockade in patients with central retinal vein occlusion that are at risk for neovascularization and in patients with severe non-proliferative diabetic retinopathy that are at risk of progressing to neovascular disease.

Alternately, the drug delivery system can be a PLGA implant, liposomal encapsulated antibodies optionally entrapped in a cross-linked hyaluronic acid. Additionally, microspheres, microcapsules (ranging from 0.001 to 100 microns) and liposomes with modified surfaces to create an interaction with the hydrogel polymer to modify release.

Also encompassed herein are particular drug delivery system formulations and methods for administering these drug delivery systems for treating an ocular condition. Intraocular administration can be by implantation or injection into the vitreous cavity (posterior chamber) of the eye. The drug delivery systems within the scope of this disclosure can be biodegradable implants and/or microspheres. The drug delivery systems can be monolithic, that is the active agent is homogenously distributed or dispersed throughout the biodegradable polymer. The therapeutic agent can be released from drug delivery systems made according to the present invention for a period of time between about 2 hours to 12 months or more. An important feature of the drug delivery systems is that they do not include any means (such as a cap, protrusion or suture tab) for fixing the drug delivery system to the intraocular location to which it is administered.

An important characteristic of a drug delivery system within the scope of the present disclosure is that it can be implanted or injected into an intraocular location (such as an anterior sub-Tenon, subconjunctival, intravitreal or suprachoroidal location) to provide sustained release of a therapeutic agent without the occurrence of or the persistence of significant immunogenicity at and adjacent to the site of the intraocular implantation or injection.

Polylactide (PLA) polymers exist in two chemical forms, poly(L-lactide) and poly(D,L-lactide). The pure poly(L-lactide) is regioregular and therefore is also highly crystalline, therefore degrades in vivo at a very slow rate. The poly(D,L-lactide) is regiorandom which leads to more rapid degradation in vivo. Therefore a PLA polymer which is a mixture of predominantly poly(L-lactide) polymer, the remainder being a poly(D-lactide) polymer will degrade in vivo at a rate slower that a PLA polymer which is predominantly poly(D-lactide) polymer. A PLGA is a copolymer that combines poly(D,L-lactide) with poly(glycolide) in various possible ratios. The higher the glycolide content in a PLGA the faster the polymer degradation.

In some embodiments, a drug delivery system for intraocular administration (i.e. by intravitreal implantation or injection) comprises configured, consists of, or consists essentially of at least a 75 weight percent of a PLA and no more than about a 25 weight percent of a poly(D,L-lactide-co-glycolide) polymer.

Also within the scope are suspensions of microspheres (incorporating an anti-neovascular agent) suspended in a hydrogel (such as a polymeric hyaluronic acid) which can be administered to an intraocular location through a syringe needle. Administration of such a suspension requires that the viscosity of the microsphere suspension at 25° C. be less than about 300,000 cP. The viscosity of water at 25° C. is about 1.0 cP (cP or cps is centipoise, a measure of viscosity). At 25° C. the viscosity of olive oil is 84 cP, of castor oil 986 cP, and of glycerol 1490 cP.

The antibodies present in the drug delivery systems can be homogeneously dispersed in the biodegradable polymer of the drug delivery system. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the drug delivery system.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked.

For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen can be present as amide, cyano, and amino. An exemplary list of biodegradable polymers that can be used are described in Heller, Biodegradable Polymers in Controlled Drug Delivery, In: "CRC Critical Reviews in Therapeutic Drug Carrier Systems", Vol. 1. CRC Press, Boca Raton, Fla. (1987).

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50/50 PLGA copolymers are used. In other variations, PLGA copolymers are used in conjunction with polylactide polymers.

Other agents may be employed in a drug delivery system formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Surfactants which can be used to stabilize particles in a colloid and/or electrolytes such as sodium chloride and potassium chloride can also be included in the formulation. The drug delivery system can also include acid and basic excipients to control pH in the microenvironment as well as at interfaces (diffusional stagnant layer).

The biodegradable drug delivery systems can also include additional hydrophilic or hydrophobic compounds that accelerate or retard release of the active agent. Additionally, release modulators such as those described in U.S. Pat. No. 5,869,079 can be included in the implants. The amount of release modulator employed will be dependent on the desired release profile, the activity of the modulator, and on the release profile of the glucocorticoid in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion.

A drug delivery system within the scope of the present disclosure can be formulated with particles of an active agent antibody dispersed within a biodegradable polymer. Without being bound by theory, it is believed that the release of the active agent can be achieved by erosion of the biodegradable polymer matrix and by diffusion of the particulate agent into an ocular fluid, e.g., the vitreous, with subsequent dissolution of the polymer matrix and release of the active agent. Factors which influence the release kinetics of active agent from the implant can include such characteristics as the size and shape of the implant, the size of the active agent particles, the solubility of the active agent, the ratio of active agent to polymer(s), the method of manufacture, the surface area exposed, the density of the implant and the erosion rate of the polymer(s).

The release rate of the active agent can depend at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release. The release rate of the active agent can also be influenced by the crystallinity of the active agent, the pH in the implant and the pH at interfaces.

The release kinetics of the drug delivery systems of the present invention can be dependent in part on the surface area of the drug delivery systems. A larger surface area exposes more polymer and active agent to ocular fluid, causing faster erosion of the polymer and dissolution of the active agent particles in the fluid.

Also disclosed herein are pharmaceutical compositions comprising a monospecific human anti-PDGF HCAb and/or a bispecific antibody in which one of the specificities is PDGF. Also disclosed is the use of the antibodies described herein for the manufacture of a pharmaceutical composition. Also disclosed are methods of using the disclosed antibodies and pharmaceutical compositions comprising the antibodies for the treatment of ocular disorders.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, intraocular, intravitreal, subcutaneous, parenteral, spinal or epidermal administration (e.g. by injection or infusion).

A composition disclosed herein can be administered by a variety of methods known in the art. As will be appreciated by the skilled artisan, the route and/or mode of administration will vary depending upon the desired results. To administer the disclosed antibodies by certain routes of administration, it may be necessary to associate the antibodies with, or co-administer the antibodies with, a material to prevent its inactivation. For example, the antibodies may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intraocular, intravitreal, intradermal, intraperitoneal, transtracheal, subcutaneous, subcuticular, intra-articular, subcapsular, subarachnoid, intraspinal, epidural, and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the disclosed antibodies, which may be used in a suitable hydrated form, and/or the pharmaceutical compositions containing the antibodies, are formulated into pharmaceutically acceptable dosage forms by conventional methods known to those of skill in the art.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Suitable doses for the pharmaceutical compositions disclosed herein when delivered intravitreally are in the range of about 0.1 mg to about 50 mg per eye. Additional suitable doses include, but are not limited to, about 0.2 mg to about 40 mg per eye, about 0.3 mg to about 30 mg per eye, about 0.4 mg to about 20 mg per eye, about 0.5 mg to about 15 mg per eye, about 0.5 mg to about 10 mg per eye, about 0.5 mg per eye, about 0.75 mg per eye, about 1 mg per eye, about 1.5 mg per eye, about 2 mg per eye, about 2.5 mg per eye, about 3 mg per eye, about 3.5 mg per eye, about 4 mg per eye, about 4.5 mg per eye, about 5 mg per eye, about 5.5 mg per eye, about 6 mg per eye, about 6.5 mg per eye, about 7 mg per eye, about 7.5 mg per eye, about 8 mg per eye, about 8.5 mg per eye, about 9 mg per eye, about 9.5 mg per eye, about 10 mg per eye, about 11 mg per eye, about 12 mg per eye, about 13 mg per eye, about 14 mg per eye, about 15 mg per eye, about 15 mg per eye, about 17 mg per eye, about 18 mg per eye, about 19 mg per eye, or about 20 mg per eye.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The pharmaceutical compositions and drug delivery systems including the monospecific and/or bispecific human anti-PDGF antibodies can be injected to an intraocular location by syringe or can be inserted (implanted) into the eye by a variety of methods, including placement by forceps, by trocar, or by other types of applicators, after making an incision in the sclera. In some instances, a trocar or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. Pat. No. 7,090,681.

The method of administration generally first involves accessing the target area within the ocular region with the needle, trocar or implantation device. Once within the target area, e.g., the vitreous cavity, a lever on a hand held device can be depressed to cause an actuator to drive a plunger forward. As the plunger moves forward, it can push the implant or implants into the target area (i.e., the vitreous).

Various techniques may be employed to make implants within the scope of the present disclosure. Useful techniques include phase separation methods, interfacial methods, extrusion methods, compression methods, molding methods, injection molding methods, heat press methods and the like.

The term "intraocular injection" refers to an injection that is administered by entering the eyeball of the patient. The term "peri-ocular injection" refers to an injection that is administered behind the eye but outside the eye wall. The term "transzonular" refers to an injection administered through the ciliary zonule which is a series of fibers connecting the ciliary body and lens of the eye. The term "intravitreal" refers to an injection administered through an eye of the patient, directly into the inner cavity of the eye.

Pharmaceutical formulations described herein can be delivered via intraocular intravitreal injection which can be transzonular, or, if desired not transzonular. Intraocular intravitreal injection of this formulation, whether done via transzonular or via direct pars plana (trans-scleral) injection, delivers potent broad spectrum antibiotics directly into the suppurative tissue without requiring the urgent compounding of multiple individual medications or multiple individual injections into the eye.

Typically, a pharmaceutical composition described above will be intraocularly administered to a mammalian subject (e.g., humans, cats, dogs, other pets, domestic, wild or farm animals) in need of treatment. The composition is to be injected intravitreally and trans-zonularly using methods and techniques known to those having ordinary skilled in the art of ophthalmology.

Typically, the delivery through a typical 27 gauge cannula can be employed utilizing a 1 mL TB syringe, with attention to re-suspending the formulation using momentary flicks and shake just prior to injection. The medicinal volume (i.e., dosage) required of this formulation varies based on the type of ocular disorder and anatomic considerations regarding the available volume for the injection being added to a closed intraocular space.

Additionally, intracameral (that is, anterior chamber) injections are within the scope of the instant disclosure.

In alternative embodiments, if desired or necessary, the formulations may also be delivered in the form of eye drops or eye sprays, as well as via subconjunctival injection, intraocular intracameral injection, sub-tenon injection, intra-articular injection or intra-lesional injection, particularly, in, but not limited to, some cases when necessary to deliver additional medication when the patient's needs warrant.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Example 1

Anti-PDGF HCAb with Murine Constant Regions

All animal procedures were performed in accordance with the guidelines established by the Institutional Animal Care and Use Committee. HCAb mice from Harbour Antibodies (Cambridge, Mass.) were used to generate the anti-PDGF antibodies.

Five female HCAb mice were initially immunized intraperitoneally with 10 µg of purified human PDGF-BB (R&D systems, Minneapolis, Minn.) and Complete Freund Adjuvant (CFA, Sigma, St. Louis, Mo.) on day 0. The mice were boosted intraperitoneally with 10 µg of purified human PDGF-BB and Incomplete Freund Adjuvant (IFA, Sigma, St. Louis, Mo.) on days 15, 30 and 45. Serum antibody titers against PDGF-BB were determined on day 60 of the immunization schedule. Three days prior to harvesting the spleens, the mice were boosted intravenously with the human PDGF-BB (10 µg/mouse). Fusions were performed according to standard hybridoma technology methods with the SP20 fusion partner. Hybridoma supernatants were screened by enzyme-linked immunosorbent assay (ELISA) to detect anti-human PDGF-BB. Positive cultures were expanded and sub-cloned twice by limiting dilution. Protein A purified antibody preparations were used in all studies.

Example 2

Anti-PDGF HCAb with Human Constant Regions

Figure 3:
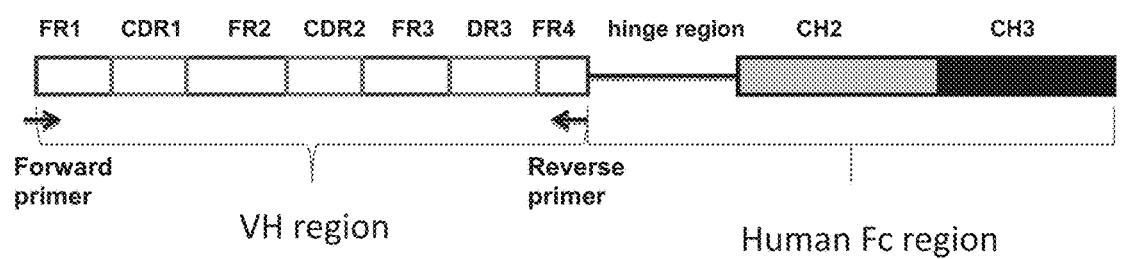
FIG. 3 depicts the gene structure of humanized HCAb disclosed herein.
Figure 4:
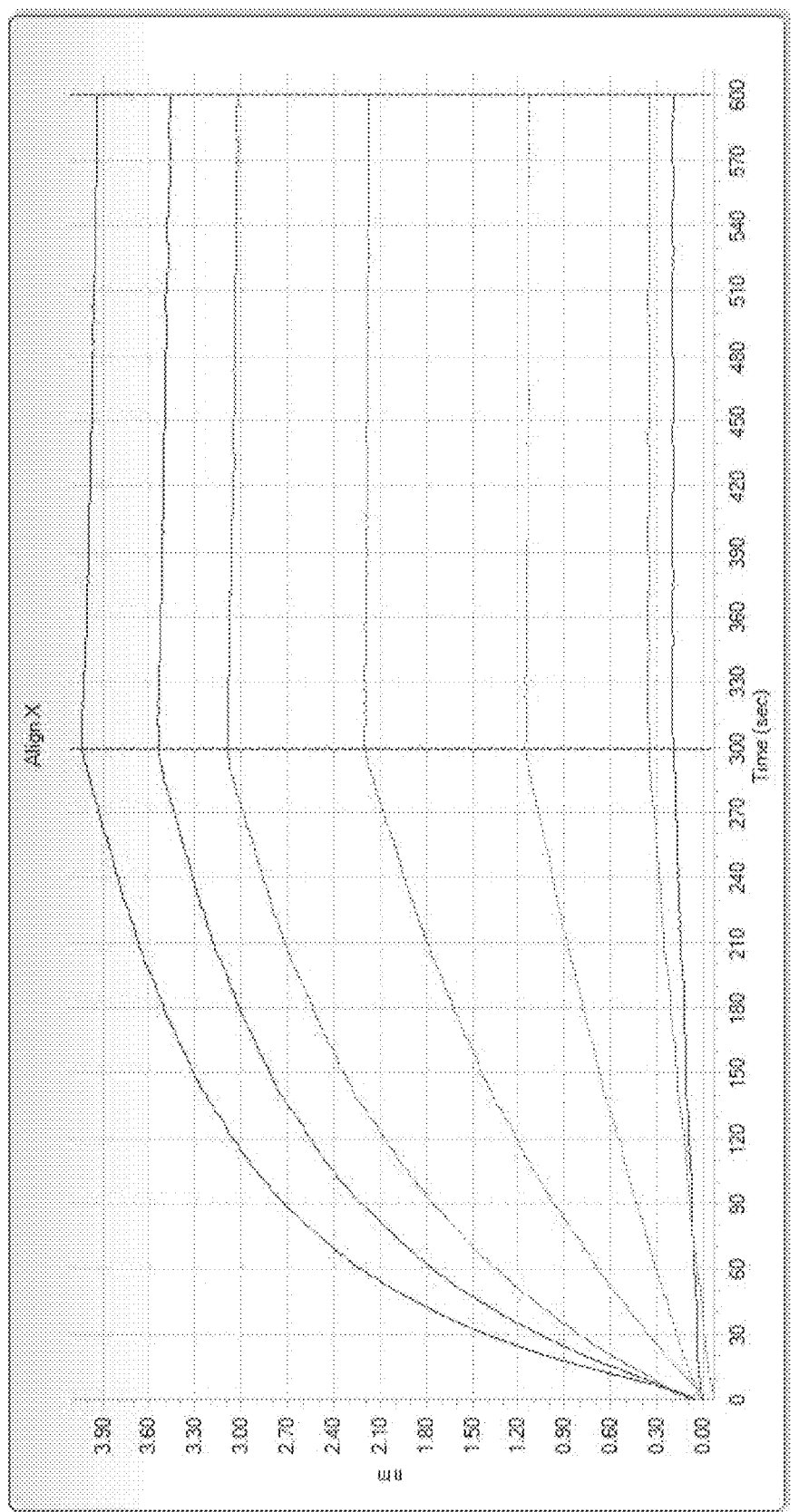
FIG. 4 depicts a binding profile analysis of an A33A8/P36F3 HCAb bispecific antibody (an example of which is shown in FIG. 2B).

Total RNA was isolated from desired hybridomas and was amplified by PCR using specific primers. The isolated VH regions from each hybridoma (FIG. 3) were fused with a LgG1 hinge region and CH2/CH3 regions to form a HCAb sequence in the GS SYSTEM™ (Lonza, Basel, Switzerland) expression plasmid. The expression plasmid was transfected into a CHO cell line to produce fully human recombinant HCAb.

Examples of human anti-PDGF HCAbs of the invention are as follows:

TABLE 2

Sequences of anti-PDGF-BB HCAbs

| Antibody Designation/Region | Sequence | SEQ ID NO: |
|---|---|---|
| P36F3 | | |
| VH | QVQLVESGGG LVQPGGSLRL SCAASGFTFS SYWMHWVRQA PGKGLVWVSR INSDGSSTSY ADSVKGRFTI SRDNAKNTLY LQMNSLRAED TAVYYCAKDK GITMVRGVIH FDYWGQGTLV TVSS | 10 |
| CDR1 | GFTFSSY | 11 |
| CDR2 | ISGSGGST | 12 |
| CDR3 | AKDKGITMVR GVIHFDY | 13 |
| P36E10 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASNS GFFTLSGFIR YKFWGQGTLV TVSS | 14 |
| CDR1 | GFTFSSY | 15 |
| CDR2 | ISGSGGST | 16 |
| CDR3 | SNSGFFTLS GFIRYKF | 17 |
| P36E8 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASNS ELFKVNGVIR YDFWGQGTLV TVSS | 18 |
| CDR1 | GFTFSSY | 19 |
| CDR2 | ISGSGGST | 20 |
| CDR3 | ASNSELFKVN GVIRYDF | 21 |
| P36C12 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCARNS EIFMVKGVIQ YNSWGQGTLV TVSS | 22 |

TABLE 2-continued

Sequences of anti-PDGF-BB HCAbs

| Antibody Designation/Region | Sequence | SEQ ID NO: |
|---|---|---|
| CDR1 | GFTFSSY | 23 |
| CDR2 | ISGSGGST | 24 |
| CDR3 | RNSEIFMVKG VIQYNS | 25 |
| P36A4 | | |
| VH | QVQLLESGGG LVQPGGSLRL SCPASGFTFS SYAMSWVRQA PGKGLEWVSA ISGSGGSTYY ADSVKGRFTI SRDNSKNTLY LQMNSLRAED TAVYYCARNN GIFMFRGVIR YKSWGQGTLV TVSS | 26 |
| CDR1 | GFTFSSY | 27 |
| CDR2 | ISGSGGST | 28 |
| CDR3 | RNNGIFMFRG VIRYKS | 29 |
| P36A3 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASNS VFSTLKGFLQ YKFWGQGTLV TVSS | 30 |
| CDR1 | GFTFSSY | 31 |
| CDR2 | ISGSGGST | 32 |
| CDR3 | SNSVFSTLKG FLQYKF | 33 |
| P36D9 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAKQR GFSMVNGLIR YKSWGQGTLV TVSS | 34 |
| CDR1 | GFTFSSY | 35 |
| CDR2 | ISGSGGST | 36 |
| CDR3 | AKQRGFSMVN GLIRYKS | 37 |
| P36E4 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASHR GFFMFNEFLR FKYWGQGTLV TVSS | 38 |
| CDR1 | GFTFSSY | 39 |
| CDR2 | ISGSGGST | 40 |
| CDR3 | ASHRGFFMFN EFLRFKY | 41 |
| P36E9 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASKR ALFRFRELFR SNYWGQGTLV TVSS | 42 |

TABLE 2-continued

Sequences of anti-PDGF-BB HCAbs

| Antibody Designation/Region | Sequence | SEQ ID NO: |
|---|---|---|
| CDR1 | GFTFSSY | 43 |
| CDR2 | ISGSGGST | 44 |
| CDR3 | ASHRGFFMFN EFLRFKY | 45 |
| P36G9 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCSRHN VISMVRALFH SHSWGQGTLV TVSS | 46 |
| CDR1 | GFTFSSY | 47 |
| CDR2 | ISGSGGST | 48 |
| CDR3 | SRHNVISMVR ALFHSHS | 49 |
| P36H4 | | |
| VH | QVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCSRES GIFKFREFIR SKYWGQGTLV TVSS | 50 |
| CDR1 | GFTFSSY | 51 |
| CDR2 | ISGSGGST | 52 |
| CDR3 | SRESGIFKFR EFIRSKY | 53 |

Example 3

Characterization of Anti-PDGF HCAb

Binding affinities and kinetic constants for antigen binding to selected purified anti-human PDGF-beta monoclonal antibodies were determined using a real-time surface plasmon resonance biosensor assay at 25° C. with a BIACORE® instrument (Biacore T200, GE Healthcare Life Sciences). Anti-human IgG Fc antibody was directly immobilized across CM5 biosensor chip (GE Healthcare) using a standard coupling kit (GE Healthcare, BR-1008-39) according to the manufacturer's instructions. Purified anti-PDGF-BB HCAb molecules were diluted in running buffer HBS-EPB (GE Healthcare, BR-1006-69) at 0.5 to 1.0 µg/ml and captured on the coupled across anti-human IgG Fc surface. A 2-fold serial dilution of human PDGF-BB (R&D system, 220-BB) range from 0.625 to 10 nM were injected over anti-PDGF-BB HCAb captured surface at a flow rate of 30 µl/min. Associating rates (Ka) and dissociation rates (Kd) were calculated based on 1:1 Langmuir binding model with BIAcore T200 evaluation software version 2.0 (GE Healthcare). The equilibrium dissociation constant (Kd) was determined by the ratio Koff/Kon. Kinetic binding parameters for different anti-PDGF BB HCAbs are shown in Table 3.

TABLE 3

Binding Characteristics of Anti-PDGF BB HCAb to Human PDGF BB

| Anti-PDGF BB HCAb | Ka (1/Ms) | Kd (1/s) | KD (M) |
|---|---|---|---|
| P36A3 | 2.19E+05 | 3.03E−07* | 1.38E−12* |
| P36A4 | 6.54E+05 | 1.17E−06 | 1.79E−12 |
| P36C12 | 1.00E+06 | 1.93E−08* | 1.92E−14* |
| P36E8 | 2.43E+05 | 1.54E−08* | 6.31E−14* |
| P36E10 | 4.21E+04 | 1.92E−05 | 4.55E−10 |
| P36F3 | 9.88E+05 | 8.73E−06 | 8.83E−12 |

*over the limit of detection

Example 4

Anti-PDGF BB HCAb Blocking of PDGF BB Binding to PDGFRβ

Two micrograms per milliliter per well of PDGFRβ-Fc (R & D Systems) was coated on 96 well microtiter plates overnight at 4° C. In a separate plate, serial dilutions of anti-PDGF BB HCAb were incubated with 2 nM human biotinylated PDGF-BB (R&D Systems) for 1 hr. One hundred microliters of the anti-PDGF BB HCAb-PDGF-BB mix were applied to the PDGFRβ-Fc-coated microtiter plate for 1 hr. The detection antibody (anti-biotin HRP) was then added for 1 hr and the ELISA was developed with a chemiluminescent HRP substrate and read by an ELISA plate reader. Anti-PDGF BB HCAb blocked the binding of PDGF-BB to its receptor PDGFRβ and $IC_{50}$ of anti-PDGF BB HCAb blocking to PDGFRβ is summarized in Table 4.

TABLE 4

Anti-PDGF BB HCAb Blocking of PDGF BB Binding to PDGFRβ

| Anti-PDGF BB HCAb | $IC_{50}$ (nM) |
|---|---|
| P36A3 | 7.75 |
| P36A4 | 3.77 |
| P36C12 | 1.07 |
| P36E8 | 5.52 |
| P36E10 | 21.39 |
| P36F3 | 1.71 |

Example 5

Characterization of Anti-PDGF HCAb

Alanine Scanning was used to identify amino acid positions in the CDR sequences that, when modified, alter the binding affinity of anti-PDGF BB HCAb P36C12.

Specific CDRs for use in the disclosed anti-PDGF BB HCAb P36C12 are presented in Table 5: underlined amino acids are those where substitution to alanine substantially decreased binding.

TABLE 5

| HC CDR1 | GFTFSS<u>Y</u> | SEQ ID NO: 23 |
|---|---|---|
| HC CDR2 | IS<u>G</u>SGG<u>ST</u> | SEQ ID NO: 24 |
| HC CDR3 | RN<u>SE</u>IFM<u>V</u>KGVIQY<u>NS</u> | SEQ ID NO: 25 |

Thus, anti-HCAb antibodies which have substitutions in certain residues of the P36C12 CDRs are within the scope of the present disclosure. In one embodiment, P36C12 CDR1 comprises GFTFSSY (SEQ ID NO:23), wherein the amino acid at position 7 is substituted with any amino acid. In other embodiments, P36C12 CDR1 comprises GFTFSSY, wherein the amino acid at position 7 is substituted with a conservative amino acid as disclosed herein. In another embodiment, P36C12 CDR1 comprises GFTFSSY, wherein the amino acid at position 7 is substituted with an amino acid of the same class as defined herein.

In one embodiment, P36C12 CDR2 comprises ISGSGGST (SEQ ID NO:24), wherein one or more of the amino acids at positions 3 or 8 are substituted with any amino acid. In other embodiments, P36C12 CDR2 comprises ISGSGGST, wherein one or more of the amino acids at positions 3 or 8 are substituted with a conservative amino acid as disclosed herein. In other embodiments, P36C12 CDR2 comprises ISGSGGST, wherein one or more of the amino acids at positions 3 or 8 are substituted with an amino acid of the same class as defined herein.

In another embodiment, P36C12 CDR3 comprises RNSEIFMVKGVIQYNS (SEQ ID NO:25), wherein one or more of the amino acids at positions 3, 4, 8, 9, 10, 11, 12, 13, 14, or 16 are substituted with any amino acid. In other embodiments, P36C12 CDR3 comprises RNSEIFMVKGVIQYNS, wherein one or more of the amino acids at positions 3, 4, 8, 9, 10, 11, 12, 13, 14, or 16 are substituted with a conservative amino acid as disclosed herein. In other embodiments, P36C12 CDR3 comprises RNSEIFMVKGVIQYNS, wherein one or more of the amino acids at positions 3, 4, 8, 9, 10, 11, 12, 13, 14, or 16 are substituted with an amino acid of the same class as defined herein.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A heavy-chain only antibody (HCAb) comprising homodimeric variable heavy chain (VH) regions where each VH region comprises:
   a CDR1 having the amino acid sequence of SEQ ID NO:23;
   a CDR2 having the amino acid sequence of SEQ ID NO:24; and
   a CDR3 having the amino acid sequence of SEQ ID NO:25;
   wherein the HCAb retains its specificity for PDGF-BB.

2. The HCAb of claim 1, wherein the VH region has at least 85% identity to SEQ ID NO:22.

3. The HCAb of claim 2, wherein the VH region has at least 90% identity to SEQ ID NO:22.

4. The HCAb of claim 2, wherein the VH region has at least 93% identity to SEQ ID NO:22.

5. The HCAb of claim 2, wherein the VH region has at least 96% identity to SEQ ID NO:22.

6. The HCAb of claim 2, wherein the VH region has at least 98% identity to SEQ ID NO:22.

7. The HCAb of claim 1, wherein the VH region comprises SEQ ID NO:22.

* * * * *

SEQUENCE LISTING

```
<160> NUMBER OF SEQ ID NOS: 58

<210> SEQ ID NO 1
<211> LENGTH: 211
<212> TYPE: PRT
<213> ORGANISM: Homo sapiens

<400> SEQUENCE: 1

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
                35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
                115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175
```

```
Cys Ala Cys Ala Thr Thr Ser Leu Asn Pro Asp Tyr Arg Glu Asp
            180                 185                 190

Thr Gly Arg Pro Arg Glu Ser Gly Lys Lys Arg Lys Arg Lys Arg Leu
            195                 200                 205

Lys Pro Thr
    210

<210> SEQ ID NO 2
<211> LENGTH: 241
<212> TYPE: PRT
<213> ORGANISM: Homo sapiens

<400> SEQUENCE: 2

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 3
<211> LENGTH: 6
<212> TYPE: PRT
<213> ORGANISM: Artificial Sequence
<220> FEATURE:
<223> OTHER INFORMATION: Synthetic linker

<400> SEQUENCE: 3

Glu Pro Lys Ser Cys Asp
1               5

<210> SEQ ID NO 4
```

```
<211> LENGTH: 6
<212> TYPE: PRT
<213> ORGANISM: Artificial Sequence
<220> FEATURE:
<223> OTHER INFORMATION: Synthetic linker

<400> SEQUENCE: 4

Ala Ser Thr Lys Gly Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic linker
<220> FEATURE:
<221> NAME/KEY: REPEAT
<222> LOCATION: (1)..(5)
<223> OTHER INFORMATION: Can be repeated up to 8 times

<400> SEQUENCE: 5

Gly Gly Gly Gly Ser
1               5

<210> SEQ ID NO 6
<211> LENGTH: 123
<212> TYPE: PRT
<213> ORGANISM: Artificial Sequence
<220> FEATURE:
<223> OTHER INFORMATION: VH of bevacizumab

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 7
<211> LENGTH: 108
<212> TYPE: PRT
<213> ORGANISM: Artificial Sequence
<220> FEATURE:
<223> OTHER INFORMATION: VL of bevacizumab

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
```

-continued

```
                35                  40                  45
Tyr Phe Thr Ser Ser Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg
             100                 105

<210> SEQ ID NO 8
<211> LENGTH: 123
<212> TYPE: PRT
<213> ORGANISM: Artificial Sequence
<220> FEATURE:
<223> OTHER INFORMATION: VH of ranibizumab

<400> SEQUENCE: 8

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Asp Phe Thr His Tyr
             20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Tyr Gly Thr Ser His Trp Tyr Phe Asp Val
             100                 105                 110

Trp Gly Gln Gly Thr Leu Val Thr Val Ser Ser
         115                 120

<210> SEQ ID NO 9
<211> LENGTH: 108
<212> TYPE: PRT
<213> ORGANISM: Artificial Sequence
<220> FEATURE:
<223> OTHER INFORMATION: VL of ranibizumab

<400> SEQUENCE: 9

Asp Ile Gln Leu Thr Gln Ser Pro Ser Ser Leu Ser Ala Ser Val Gly
  1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg
             100                 105
```

<210> SEQ ID NO 10
<211> LENGTH: 124
<212> TYPE: PRT
<213> ORGANISM: Artificial Sequence
<220> FEATURE:
<223> OTHER INFORMATION: P36F3 VL

<400> SEQUENCE: 10

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Gly Ile Thr Met Val Arg Gly Val Ile His Phe Asp
            100                 105                 110

Tyr Trp Gly Gln Gly Thr Leu Val Thr Val Ser Ser
        115                 120
```

<210> SEQ ID NO 11
<211> LENGTH: 7
<212> TYPE: PRT
<213> ORGANISM: Artificial Sequence
<220> FEATURE:
<223> OTHER INFORMATION: P36F3 CDR1

<400> SEQUENCE: 11

```
Gly Phe Thr Phe Ser Ser Tyr
1               5
```

<210> SEQ ID NO 12
<211> LENGTH: 8
<212> TYPE: PRT
<213> ORGANISM: Artificial Sequence
<220> FEATURE:
<223> OTHER INFORMATION: P36F3 CDR2

<400> SEQUENCE: 12

```
Ile Ser Gly Ser Gly Gly Ser Thr
1               5
```

<210> SEQ ID NO 13
<211> LENGTH: 17
<212> TYPE: PRT
<213> ORGANISM: Artificial Sequence
<220> FEATURE:
<223> OTHER INFORMATION: P36F3 CDR3

<400> SEQUENCE: 13

```
Ala Lys Asp Lys Gly Ile Thr Met Val Arg Gly Val Ile His Phe Asp
1               5                   10                  15

Tyr
```

<210> SEQ ID NO 14
<211> LENGTH: 124
<212> TYPE: PRT

```
<213> ORGANISM: Artificial Sequence
<220> FEATURE:
<223> OTHER INFORMATION: P36E10 VH

<400> SEQUENCE: 14

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Ser Gly Phe Phe Thr Leu Ser Gly Phe Ile Arg Tyr Lys
            100                 105                 110

Phe Trp Gly Gln Gly Thr Leu Val Thr Val Ser Ser
        115                 120

<210> SEQ ID NO 15
<211> LENGTH: 7
<212> TYPE: PRT
<213> ORGANISM: Artificial Sequence
<220> FEATURE:
<223> OTHER INFORMATION: P36E10 CDR1

<400> SEQUENCE: 15

Gly Phe Thr Phe Ser Ser Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: P36E10 CDR2

<400> SEQUENCE: 16

Ile Ser Gly Ser Gly Gly Ser Thr
1               5

<210> SEQ ID NO 17
<211> LENGTH: 16
<212> TYPE: PRT
<213> ORGANISM: Artificial Sequence
<220> FEATURE:
<223> OTHER INFORMATION: P36E10 CDR3

<400> SEQUENCE: 17

Ser Asn Ser Gly Phe Phe Thr Leu Ser Gly Phe Ile Arg Tyr Lys Phe
1               5                   10                  15

<210> SEQ ID NO 18
<211> LENGTH: 124
<212> TYPE: PRT
<213> ORGANISM: Artificial Sequence
<220> FEATURE:
<223> OTHER INFORMATION: P36E8 VH

<400> SEQUENCE: 18
```

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Ser Glu Leu Phe Lys Val Asn Gly Val Ile Arg Tyr Asp
            100                 105                 110

Phe Trp Gly Gln Gly Thr Leu Val Thr Val Ser Ser
            115                 120
```

<210> SEQ ID NO 19
<211> LENGTH: 7
<212> TYPE: PRT
<213> ORGANISM: Artificial Sequence
<220> FEATURE:
<223> OTHER INFORMATION: P36E8 CDR1

<400> SEQUENCE: 19

```
Gly Phe Thr Phe Ser Ser Tyr
1               5
```

<210> SEQ ID NO 20
<211> LENGTH: 8
<212> TYPE: PRT
<213> ORGANISM: Artificial Sequence
<220> FEATURE:
<223> OTHER INFORMATION: P36E8 CDR2

<400> SEQUENCE: 20

```
Ile Ser Gly Ser Gly Gly Ser Thr
1               5
```

<210> SEQ ID NO 21
<211> LENGTH: 17
<212> TYPE: PRT
<213> ORGANISM: Artificial Sequence
<220> FEATURE:
<223> OTHER INFORMATION: P36E8 CDR3

<400> SEQUENCE: 21

```
Ala Ser Asn Ser Glu Leu Phe Lys Val Asn Gly Val Ile Arg Tyr Asp
1               5                   10                  15

Phe
```

<210> SEQ ID NO 22
<211> LENGTH: 124
<212> TYPE: PRT
<213> ORGANISM: Artificial Sequence
<220> FEATURE:
<223> OTHER INFORMATION: P36C12 VH

<400> SEQUENCE: 22

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Ser Glu Ile Phe Met Val Lys Gly Val Ile Gln Tyr Asn
            100                 105                 110

Ser Trp Gly Gln Gly Thr Leu Val Thr Val Ser Ser
        115                 120

<210> SEQ ID NO 23
<211> LENGTH: 7
<212> TYPE: PRT
<213> ORGANISM: Artificial Sequence
<220> FEATURE:
<223> OTHER INFORMATION: P36C12 CDR1

<400> SEQUENCE: 23

Gly Phe Thr Phe Ser Ser Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: P36C12 CDR2

<400> SEQUENCE: 24

Ile Ser Gly Ser Gly Gly Ser Thr
1               5

<210> SEQ ID NO 25
<211> LENGTH: 16
<212> TYPE: PRT
<213> ORGANISM: Artificial Sequence
<220> FEATURE:
<223> OTHER INFORMATION: P36C12 CDR3

<400> SEQUENCE: 25

Arg Asn Ser Glu Ile Phe Met Val Lys Gly Val Ile Gln Tyr Asn Ser
1               5                   10                  15

<210> SEQ ID NO 26
<211> LENGTH: 124
<212> TYPE: PRT
<213> ORGANISM: Artificial Sequence
<220> FEATURE:
<223> OTHER INFORMATION: P36A4 VH

<400> SEQUENCE: 26

Gln Val Gln Leu Leu Glu Ser Gly Gly Gly Leu Val Gln Pro Gly Gly
1               5                   10                  15

Ser Leu Arg Leu Ser Cys Pro Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asn Asn Gly Ile Phe Met Phe Arg Gly Val Ile Arg Tyr Lys
                100                 105                 110

Ser Trp Gly Gln Gly Thr Leu Val Thr Val Ser Ser
            115                 120
```

<210> SEQ ID NO 27
<211> LENGTH: 7
<212> TYPE: PRT
<213> ORGANISM: Artificial Sequence
<220> FEATURE:
<223> OTHER INFORMATION: P36A4 CDR1

<400> SEQUENCE: 27

```
Gly Phe Thr Phe Ser Ser Tyr
 1               5
```

<210> SEQ ID NO 28
<211> LENGTH: 8
<212> TYPE: PRT
<213> ORGANISM: Artificial Sequence
<220> FEATURE:
<223> OTHER INFORMATION: P36A4 CDR2

<400> SEQUENCE: 28

```
Ile Ser Gly Ser Gly Gly Ser Thr
 1               5
```

<210> SEQ ID NO 29
<211> LENGTH: 16
<212> TYPE: PRT
<213> ORGANISM: Artificial Sequence
<220> FEATURE:
<223> OTHER INFORMATION: P36A4 CDR3

<400> SEQUENCE: 29

```
Arg Asn Asn Gly Ile Phe Met Phe Arg Gly Val Ile Arg Tyr Lys Ser
 1               5                  10                  15
```

<210> SEQ ID NO 30
<211> LENGTH: 124
<212> TYPE: PRT
<213> ORGANISM: Artificial Sequence
<220> FEATURE:
<223> OTHER INFORMATION: P36A3 VH

<400> SEQUENCE: 30

```
Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                    85                  90                  95
Ala Ser Asn Ser Val Phe Ser Thr Leu Lys Gly Phe Leu Gln Tyr Lys
            100                 105                 110

Phe Trp Gly Gln Gly Thr Leu Val Thr Val Ser Ser
        115                 120

<210> SEQ ID NO 31
<211> LENGTH: 7
<212> TYPE: PRT
<213> ORGANISM: Artificial Sequence
<220> FEATURE:
<223> OTHER INFORMATION: P36A3 CDR1

<400> SEQUENCE: 31

Gly Phe Thr Phe Ser Ser Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: P36A3 CDR2

<400> SEQUENCE: 32

Ile Ser Gly Ser Gly Gly Ser Thr
1               5

<210> SEQ ID NO 33
<211> LENGTH: 16
<212> TYPE: PRT
<213> ORGANISM: Artificial Sequence
<220> FEATURE:
<223> OTHER INFORMATION: P36A3 CDR3

<400> SEQUENCE: 33

Ser Asn Ser Val Phe Ser Thr Leu Lys Gly Phe Leu Gln Tyr Lys Phe
1               5                   10                  15

<210> SEQ ID NO 34
<211> LENGTH: 124
<212> TYPE: PRT
<213> ORGANISM: Artificial Sequence
<220> FEATURE:
<223> OTHER INFORMATION: P36D9 VH

<400> SEQUENCE: 34

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Arg Gly Phe Ser Met Val Asn Gly Leu Ile Arg Tyr Lys
            100                 105                 110

Ser Trp Gly Gln Gly Thr Leu Val Thr Val Ser Ser
        115                 120
```

<210> SEQ ID NO 35
<211> LENGTH: 7
<212> TYPE: PRT
<213> ORGANISM: Artificial Sequence
<220> FEATURE:
<223> OTHER INFORMATION: P36D9 CDR1

<400> SEQUENCE: 35

Gly Phe Thr Phe Ser Ser Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: P36D9 CDR2

<400> SEQUENCE: 36

Ile Ser Gly Ser Gly Gly Ser Thr
1               5

<210> SEQ ID NO 37
<211> LENGTH: 17
<212> TYPE: PRT
<213> ORGANISM: Artificial Sequence
<220> FEATURE:
<223> OTHER INFORMATION: P36D9 CDR3

<400> SEQUENCE: 37

Ala Lys Gln Arg Gly Phe Ser Met Val Asn Gly Leu Ile Arg Tyr Lys
1               5                   10                  15

Ser

<210> SEQ ID NO 38
<211> LENGTH: 124
<212> TYPE: PRT
<213> ORGANISM: Artificial Sequence
<220> FEATURE:
<223> OTHER INFORMATION: P36E4 VH

<400> SEQUENCE: 38

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Arg Gly Phe Phe Met Phe Asn Glu Phe Leu Arg Phe Lys
            100                 105                 110

Tyr Trp Gly Gln Gly Thr Leu Val Thr Val Ser Ser
        115                 120

<210> SEQ ID NO 39

```
<211> LENGTH: 7
<212> TYPE: PRT
<213> ORGANISM: Artificial Sequence
<220> FEATURE:
<223> OTHER INFORMATION: P36E4 CDR1

<400> SEQUENCE: 39

Gly Phe Thr Phe Ser Ser Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: P36E4 CDR2

<400> SEQUENCE: 40

Ile Ser Gly Ser Gly Gly Ser Thr
1               5

<210> SEQ ID NO 41
<211> LENGTH: 17
<212> TYPE: PRT
<213> ORGANISM: Artificial Sequence
<220> FEATURE:
<223> OTHER INFORMATION: P36E4 CDR3

<400> SEQUENCE: 41

Ala Ser His Arg Gly Phe Phe Met Phe Asn Glu Phe Leu Arg Phe Lys
1               5                   10                  15

Tyr

<210> SEQ ID NO 42
<211> LENGTH: 124
<212> TYPE: PRT
<213> ORGANISM: Artificial Sequence
<220> FEATURE:
<223> OTHER INFORMATION: P36E9 VH

<400> SEQUENCE: 42

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Lys Arg Ala Leu Phe Arg Phe Arg Glu Leu Phe Arg Ser Asn
            100                 105                 110

Tyr Trp Gly Gln Gly Thr Leu Val Thr Val Ser Ser
        115                 120

<210> SEQ ID NO 43
<211> LENGTH: 7
<212> TYPE: PRT
<213> ORGANISM: Artificial Sequence
<220> FEATURE:
```

<223> OTHER INFORMATION: P36E9 CDR1

<400> SEQUENCE: 43

Gly Phe Thr Phe Ser Ser Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: P36E9 CDR2

<400> SEQUENCE: 44

Ile Ser Gly Ser Gly Gly Ser Thr
1               5

<210> SEQ ID NO 45
<211> LENGTH: 17
<212> TYPE: PRT
<213> ORGANISM: Artificial Sequence
<220> FEATURE:
<223> OTHER INFORMATION: P36G9 CDR3

<400> SEQUENCE: 45

Ala Ser His Arg Gly Phe Phe Met Phe Asn Glu Phe Leu Arg Phe Lys
1               5                   10                  15

Tyr

<210> SEQ ID NO 46
<211> LENGTH: 124
<212> TYPE: PRT
<213> ORGANISM: Artificial Sequence
<220> FEATURE:
<223> OTHER INFORMATION: P36G9 VH

<400> SEQUENCE: 46

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg His Asn Val Ile Ser Met Val Arg Ala Leu Phe His Ser His
            100                 105                 110

Ser Trp Gly Gln Gly Thr Leu Val Thr Val Ser Ser
        115                 120

<210> SEQ ID NO 47
<211> LENGTH: 7
<212> TYPE: PRT
<213> ORGANISM: Artificial Sequence
<220> FEATURE:
<223> OTHER INFORMATION: P36G9 CDR1

<400> SEQUENCE: 47

Gly Phe Thr Phe Ser Ser Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: P36G9 CDR2

<400> SEQUENCE: 48

Ile Ser Gly Ser Gly Gly Ser Thr
1               5

<210> SEQ ID NO 49
<211> LENGTH: 17
<212> TYPE: PRT
<213> ORGANISM: Artificial Sequence
<220> FEATURE:
<223> OTHER INFORMATION: P36G9 CDR3

<400> SEQUENCE: 49

Ser Arg His Asn Val Ile Ser Met Val Arg Ala Leu Phe His Ser His
1               5                   10                  15

Ser

<210> SEQ ID NO 50
<211> LENGTH: 124
<212> TYPE: PRT
<213> ORGANISM: Artificial Sequence
<220> FEATURE:
<223> OTHER INFORMATION: P36H4 VH

<400> SEQUENCE: 50

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Glu Ser Gly Ile Phe Lys Phe Arg Glu Phe Ile Arg Ser Lys
            100                 105                 110

Tyr Trp Gly Gln Gly Thr Leu Val Thr Val Ser Ser
        115                 120

<210> SEQ ID NO 51
<211> LENGTH: 7
<212> TYPE: PRT
<213> ORGANISM: Artificial Sequence
<220> FEATURE:
<223> OTHER INFORMATION: P36H4 CDR1

<400> SEQUENCE: 51

Gly Phe Thr Phe Ser Ser Tyr
1               5

```
<210> SEQ ID NO 52
<211> LENGTH: 8
<212> TYPE: PRT
<213> ORGANISM: Artificial Sequence
<220> FEATURE:
<223> OTHER INFORMATION: P36H4 CDR2

<400> SEQUENCE: 52

Ile Ser Gly Ser Gly Gly Ser Thr
1               5

<210> SEQ ID NO 53
<211> LENGTH: 17
<212> TYPE: PRT
<213> ORGANISM: Artificial Sequence
<220> FEATURE:
<223> OTHER INFORMATION: P36H4 CDR3

<400> SEQUENCE: 53

Ser Arg Glu Ser Gly Ile Phe Lys Phe Arg Glu Phe Ile Arg Ser Lys
1               5                   10                  15

Tyr

<210> SEQ ID NO 54
<211> LENGTH: 120
<212> TYPE: PRT
<213> ORGANISM: Artificial Sequence
<220> FEATURE:
<223> OTHER INFORMATION: A33A8 VH

<400> SEQUENCE: 54

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Gly Gln Phe Asp Tyr Trp Gly Gln
            100                 105                 110

Gly Thr Leu Val Thr Val Ser Ser
        115                 120

<210> SEQ ID NO 55
<211> LENGTH: 120
<212> TYPE: PRT
<213> ORGANISM: Artificial Sequence
<220> FEATURE:
<223> OTHER INFORMATION: A1G2 VH

<400> SEQUENCE: 55

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45
```

Ser Arg Ile Asn Ser Asp Gly Ser Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ser Ser Glu Gly Phe Ser Ser Gly Glu His Ser Glu Phe Trp Gly Gln
            100                 105                 110

Gly Thr Leu Val Thr Val Ser Ser
            115                 120

<210> SEQ ID NO 56
<211> LENGTH: 120
<212> TYPE: PRT
<213> ORGANISM: Artificial Sequence
<220> FEATURE:
<223> OTHER INFORMATION: A1F8 VH

<400> SEQUENCE: 56

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Val Trp Val
         35                  40                  45

Ser Arg Ile Asn Ser Asp Gly Ser Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ser Ser Glu Gly Tyr Ser Ser Glu Ala His Ser Glu Gln Tyr Trp Gly Gln
            100                 105                 110

Gly Thr Leu Val Thr Val Ser Ser
            115                 120

<210> SEQ ID NO 57
<211> LENGTH: 120
<212> TYPE: PRT
<213> ORGANISM: Artificial Sequence
<220> FEATURE:
<223> OTHER INFORMATION: A2B6 VH

<400> SEQUENCE: 57

Gln Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ala Ala Tyr
             20                  25                  30

Trp Met His Trp Val Arg Gln Ala Pro Gly Lys Gly Leu Val Trp Val
         35                  40                  45

Ser Arg Ile Asn Ser Asp Gly Ser Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Ser Gly Gly Gln Phe Asp Tyr Trp Gly Gln

```
<210> SEQ ID NO 58
<211> LENGTH: 120
<212> TYPE: PRT
<213> ORGANISM: Artificial Sequence
<220> FEATURE:
<223> OTHER INFORMATION: A1B1 VH

<400> SEQUENCE: 58

Gln Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Tyr Ala Ala Phe
            20                  25                  30

Trp Met Ser Trp Val Arg Gln Ala Pro Gly Lys Gly Leu Glu Trp Val
        35                  40                  45

Ser Ala Ile Asn Ser Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Gly Gly Gln Phe Asp Tyr Trp Gly Gln
            100                 105                 110

Gly Thr Leu Val Thr Val Ser Ser
        115                 120
```